United States Patent [19]
Morgan

[11] Patent Number: 5,346,492
[45] Date of Patent: Sep. 13, 1994

[54] PERFORATED METALLIC PANELS AND STRIPS FOR INTERNAL FIXATION OF BONE FRACTURES AND FOR RECONSTRUCTIVE SURGERY

[75] Inventor: Frank H. Morgan, Las Vegas, Nev.

[73] Assignee: TiMesh, Inc., Las Vegas, Nev.

[21] Appl. No.: 28,207

[22] Filed: Mar. 9, 1993

Related U.S. Application Data

[63] Continuation-in-part of Ser. No. 860,029, Mar. 30, 1992, abandoned.

[51] Int. Cl.$^5$ ............................................. A61F 2/28
[52] U.S. Cl. ...................................... 606/60; 606/69; 623/16; 411/461
[58] Field of Search ............ 52/85, DIG. 6; 411/457, 411/461, 537, 379, 380, 381; 606/60, 61, 69-73, 76, 105; 623/16

[56] References Cited

U.S. PATENT DOCUMENTS

| | | | |
|---|---|---|---|
| 1,105,105 | 7/1914 | Sherman | 606/69 |
| 4,905,679 | 3/1990 | Morgan | 606/70 |
| 4,923,471 | 5/1990 | Morgan | 623/16 |
| 5,129,899 | 7/1992 | Small et al. | 606/61 |
| 5,139,497 | 8/1992 | Tilghman et al. | 606/69 |
| 5,290,281 | 3/1994 | Tschakaloff | 606/69 |

*Primary Examiner*—Randall L. Green
*Assistant Examiner*—Mary Beth Jones
*Attorney, Agent, or Firm*—Philip D. Junkins

[57] ABSTRACT

A pliable metallic mesh implant plate structure for the internal fixation of bone fractures and for use in orthognathic and reconstructive surgery. The plate structure includes a multiplicity of substantially square perforations extending from the outer face side of the plate structure to the bone interface side thereof and arranged uniformly in parallel rows and parallel lines. Each perforation includes an arcuate chamfer of substantially uniform configuration extending inwardly from the outer face side of the plate structure to the bone interface side about the entire periphery thereof. Thus, when bone screws, having a screw head configuration including a hemispherical underside portion and a low profile upper head portion, are applied through the perforations of the mesh plate structure from the outer face side and screwed into bone proximate the bone interface side thereof, with the screw heads seated in congruent fitment in the perforation, there is presented a relatively non-obtrusive surface at the face side of the plate structure.

4 Claims, 1 Drawing Sheet

PERFORATED METALLIC PANELS AND STRIPS FOR INTERNAL FIXATION OF BONE FRACTURES AND FOR RECONSTRUCTIVE SURGERY

This is a continuation-in-part of my co-pending application Ser. No. 07/860,029 filed Mar. 30, 1992, now abandoned.

FIELD OF THE INVENTION

The present invention relates to perforated metallic panels and strips for use in orthognathic and reconstructive surgery and for rigid internal fixation of fractures in trauma surgery.

BACKGROUND OF THE INVENTION

A bone fracture is a traumatic disruption of the continuity of a bone. If there is relative motion of the bone fragments at the fracture site irritation of the surrounding tissues and heavy pain ensue and the time of fracture healing is usually extended. Proper rejoinder of bone fragments is thus dependent upon the immobilization of the fracture site. Classically, bone fragment reduction (bone fragments properly aligned and abutted along the fracture line) and immobilization for fractured limb bones has been accomplished by external limb casts. Such casts must be worn for long periods of time, are heavy and unbalancing to the body skeletal structure and muscular system, inhibit bone vascularity (promotes fast and effective bone healing), and may result in bone resorption because of the total absence of tensile and compressive functional force loading throughout the fractured bone structure. Fractures in bones other than the arms and legs are more difficult to immobilize and the use of exterior casts may not be possible.

Over the past twenty-five years the use of compression plate techniques for internal fixation of fractures have been developed and widely applied. With internal fixation, by means of bone screws and compression plates, particularly plates made of biocompatible metals and metal alloys (such as titanium and stainless steel), immediate and absolute immobilization is achieved through interfragmentary compression. Other materials and devices such as wires, intramedullary nails or externally fixed pins are used mainly to reduce bone fracture mobility and improve the position of the fracture segments. The basic aim of internal bone fracture fixation is to allow early, pain-free movement of the injured limb, mandible, etc., thus avoiding the consequences of long lasting immobilization, i.e., bone fracture disease, bone resorption, etc.

In addition to the use of bone screws and compression plates to effectively accomplish internal bone fracture fixation, implantable biocompatible metallic plates are being increasingly used in oral and maxillofacial surgery to effect the surgical correction of craniofacial anomalies. Craniofacial surgery requires the use of both compression and non-compression plates. Thus, in orthognathic procedures, is may not be desirable to compress an osteotomy. Also, midfacial trauma injuries are frequently treated through the use of non-compression bone fixation plates.

With internal bone fixation it is important that the application of the implanted plate or fracture reduction device result in relative immobility of the bone fragments (fracture situations) or surgically prepared bone parts (reconstruction situations) and tight closure of the bone interfaces. Without such immobility and tight closure, changing tension and compression loads tend to produce relative motion at the bone interfaces with resultant undesirable bone fragment or bone part shortening due to bone resorption. Through the proper use of a biocompatible metallic bone stabilization plate or fracture reduction device (a surgically applied implant), static forces applied by the plate or device prevent relative motion between the bone interface surfaces. Thus, complete immobilization and stabilization of the bone fragments or bone parts (through the plate or device) prevents relative motion at the bone interfaces in spite of functional use of the limb, mandible, etc., without external immobilization or splinting. With mechanical stimuli (forces and motion) permitted via internal bone fixation techniques, rapid and healthy healing of a fracture or surgical reconstruction is promoted and bone vascularity is maintained and restored. Vascularity of bone is interrupted by the fracture trauma and by surgical intervention but revascularization is restored and enhanced by the rigid immobilization of the bone fragment or bone part interfaces through internal fixation techniques.

Further developments in compression and non-compression bone fixation plate designs and attachment screws (also formed of biocompatible metals and metal alloys) have related to screw head and screw hole geometry, i.e., conical geometry of the screw shoulder and oval screw holes in the fixation plate for promoting bone fragment compression during screw application. Attempts to obtain optimal stability of fixation have most recently resulted in the use of congruent fitment between the underside of the head of bone screws and the screw holes in the fixation plate including both counter-sunk holes (conical geometry) and hemicylinderical holes. Also, the development of low head profiles for bone screws has permitted the use of implantable bone plates in fixation situations directly below soft tissue body surfaces without causing cosmetic appearance abnormalities or creating an uneven and irritating surface characteristic of such plates otherwise caused by screw heads.

Over the past ten years there has been an increasing interest in, and use of, perforated biocompatible metallic strips and panels as a means for rigid internal fixation of fractures in trauma surgery and as a plate material for bone part immobilization and stabilization and bone graft support material in orthognathic and reconstructive surgery. Of particular interest has been the use of perforated strips and panels fabricated of titanium as an unequaled implant material in use clinically for over 30 years with no documented cases of allergic reactions. Pure titanium is the material of choice in craniofacial reconstructive surgery when non-removal of the implant is indicated. As an implant material, pure titanium is preferred because its low density (weight) and elastic modulus (stiffness) are approximately one-half that of stainless steel or cobalt-chromium alloys and the material is corrosion resistant and pliable. Bone plates made from perforated titanium strips and perforated titanium panels can be cut to appropriate configuration and contoured at the time of surgery and, when affixed to bone fragments or bone parts with bone screws, provide solid, stable fixation means during trauma surgery and planned reconstructive surgery.

A preferred form of perforated titanium strips and panels (titanium mesh) includes rows of substantially square perforations which are formed in titanium sheet material by mechanical means (stamping and machining), by electrical arc cutting, and by milling means which preserve the stress free condition of the sheet material. The use of titanium mesh with square holes for internal fixation of bone fractures and for reconstructive surgery provides the surgeon with an implantable plate material which can be easily cut to desired contour and shaped or bent to conform to bone fracture and reconstruction sites without inducing mechanical stresses into the material because the formability of such mesh is equal along each of the legs defining each of the square holes. Also, as a perforated sheet material the plate structure provides the surgeon with a multiplicity of ready-made holes through which bone screws can be seated and applied to fasten the plate structure to bone fragments and parts. Bending of the perforated sheet material does not distort the square holes to the extent that bone screws can not be applied. This is not the case with mesh implant structures wherein the perforations are round holes. While perforated titanium implant strips and panels of the type described (square holes) provide the trauma and reconstructive surgeon with a highly desirable bone fixation plate structure, such panels and strips have in the past required that the screws applied through the plate structure have their head portions extend above the outer plate surface. Although in many internal bone fixation and reconstructive situations screw head protrusion is not an objectionable factor and causes no problem with respect to the healing process following surgery, where the implanted plate structure is at or near the body surface the protrusion of screw heads may be noticeable and irritating.

It is a principal object of the present invention to provide a unique perforated metallic plate structure for the internal fixation of fractures and for use in orthognathic and reconstructive surgery.

It is a further object of the invention to provide a unique metallic plate structure, including a multiplicity of chamfered square perforations for receiving bone screws, for use in orthognathic and reconstructive surgery and for rigid internal fixation of bone fractures in trauma surgery.

It is still a further object of the invention to provide unique perforated metallic panels and strips for use in orthognathic and reconstructive surgery and for rigid internal fixation of bone fractures with the panel and strip perforations comprising a multiplicity of substantially square chamfered holes arranged in rows and lines.

It is yet another object of the present invention to provide a unique perforated metallic plate structure, including arcuately chamfered square screw holes, for use in orthognathic and reconstructive surgery and for rigid internal fixation of bone fractures without the significant protrusion of the head portion of bone screws applied through such screw holes into the bone fragments or parts to which the plate structure is attached.

It is still another object of the invention to provide unique perforated metallic panels and strips for use in orthognathic and reconstructive surgery and for rigid internal fixation of bone fractures with the panel and strip perforations comprising a multiplicity of substantially square holes which are arcuately chamfered for receiving the hemispherical underside of low profile bone screws.

Other objects and advantages of the invention will be apparent from the following summary and detailed description of the bone fracture and bone reconstruction fixation plate structure of the invention taken together with the accompanying drawing figures.

SUMMARY OF THE INVENTION

The present invention relates to improved perforated strips and panels of biocompatible metallic sheet material for use in the internal fixation of bone fractures and for use in orthognathic and reconstructive surgery. The implantable metallic strips and panels of the invention are fabricated of biocompatible metals and metal alloys selected from the group consisting of titanium, titanium alloys, cobalt-chrome alloys and stainless steel (preferably fabricated from pure titanium) and include uniform rows and lines of arcuately chamfered square holes for receiving, in congruent fitment, the hemispherical underside of bone screws having low profile heads. The square hole perforations, with inward arcuate chamfered entry configuration, are created by milling techniques that result in the finished perforated strips and panels being free of mechanically induced stresses as are normally created by metal stamping, forging and mechanical machining procedures. The inward arcuate chamfer of each square hole is substantially uniform in arc configuration about the entire periphery of the hole, Thus, the chamfer is not merely the chamfer that would be created by a spherical mechanical burr or chamfer tool applied to a square hole resulting in a partial hemispherical chamfer only along the middle areas of each of the legs defining the square hole and no chamfer at the corners of the hole.

The use of perforated titanium strips and panels with square holes for the internal fixation of bone fractures and for reconstructive surgery provides the surgeon with an implantable plate material which can be easily cut to desired contour and shaped or bent to conform to bone fracture and bone reconstruction sites without inducing mechanical stresses into the material. Also, as a pliable perforated sheet material, the strip and panel structures of the invention provide the surgeon with a plate material having a multiplicity of ready-made holes through which bone screws having a low profile head (with a hemispherical underside) can be seated and applied to fasten the plate structure to bone fragments and parts without the protrusion of screw heads.

BRIEF DESCRIPTION OF THE DRAWING FIGURES

FIG. 1 is an oversized top plan view of a perforated metallic strip of implantable bone fracture reduction and bone reconstruction plate material in accordance with the present invention; and FIG. 2 is an enlarged cross-sectional view of the perforated metallic strip of FIG. 1 taken along line 2—2 of FIG. 1 showing the inward arcuate chamfer contour of the square screw holes of the strip and the congruent seating in one of such holes of a low profile bone screw.

DETAILED DESCRIPTION OF THE INVENTION

Figure 1:
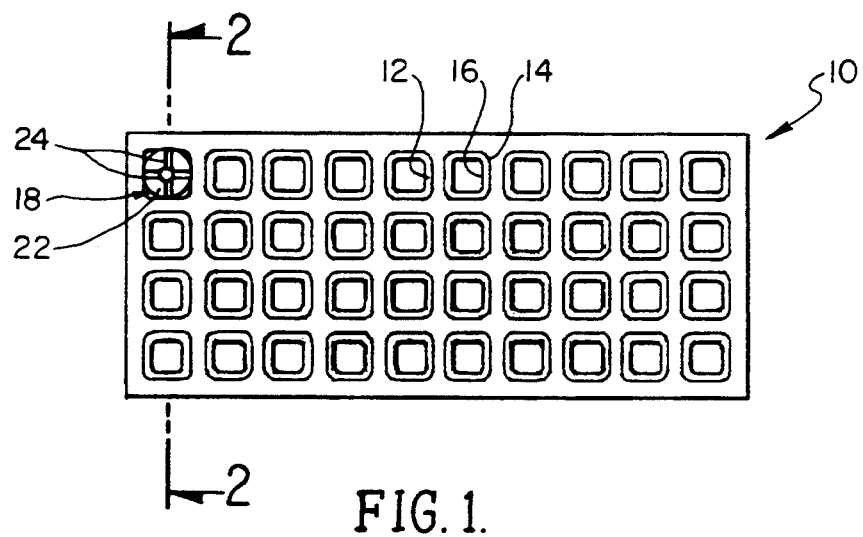
Figure 2:
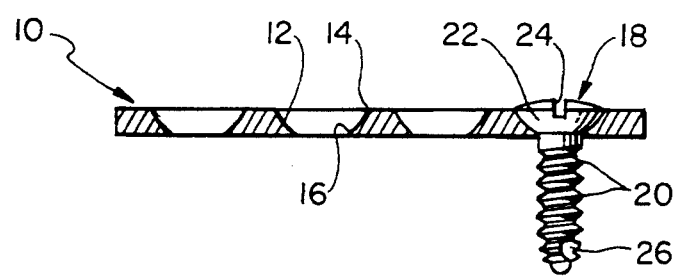

Referring to FIGS. 1 and 2 of the drawing sheet, there is illustrated an improved perforated strip of biocompatible metallic sheet material 10, in accordance with the invention, for use in the internal fixation of bone fractures and for use in orthognathic and reconstructive surgery. The implantable perforated strip 10 is fabricated from a sheet of relatively thin (stress free) metal or metal alloy (preferably titanium, titanium alloys, cobalt-chrome alloys or stainless steel). The strip perforations 12 comprise substantially square holes arranged in rows and lines to form a uniform mesh of bone plate material. The square perforations 12 of the strip 10 are chamfered in substantially uniform arcuate configuration about their entire periphery inwardly from the upper opening edge 14 of each perforation to the lower opening edge 16 thereof.

The square perforations 12 of the implantable strip 10 are created by milling procedures which preserve the stress free condition of the original metallic sheet material from which the strip is fabricated and such perforations are configured to receive in congruent fitment low profile head bone screws. An example of such a screw is shown in FIGS. 1 and 2 as self-tapping screw 18 which includes a threaded shank 20 and a screw head 22 having a hemispherical underside portion, a low profile upper head portion and cruciform slots 24 for receiving an appropriate screwdriver tip (not shown). Congruent fitment of the hemispherical underside of the screw head 22 of the screw 18 is shown with respect to the arcuate chamfer of the square perforation 12 of the strip 10. The self-tapping screw 18 also includes a fluted tip portion 26 which improves the bone cutting action of the screw during its insertion into bone.

Implantable perforated strips of the type described above (particularly suitable for orthognathic and reconstructive surgery) may be preferably fabricated, in accordance with the invention, in five inch lengths with 1 to 4 lines of perforations in widths of from 3/16 inch (one line of square holes) to 11/16 inch (four lines of square holes). Such strips, preferably formed from unalloyed commercially pure titanium sheet material with a yield strength in the range of 30,000 to 40,000 psi, have a finished thickness of from about 1 mm to about 1.5 mm. Perforated panels may be preferably fabricated from like sheet titanium material in a size of 3 and ¼ inch width and 5 and ¼ inch length.

Example: A perforated metallic strip for use in orthognathic and reconstructive surgery and for rigid internal fixation of fractures in trauma surgery, of the type illustrated in FIGS. 1 and 2, has been fabricated from unalloyed commercially pure titanium with a yield strength in the range of 30,000 to 40,000 psi. The strip (having a thickness of 1 mm, a width of ½ inch and length of 5 inches, and including 3 lines of arcuately chamfered square perforations arranged uniformly in 30 rows) was utilized after appropriate contouring and shaping to reduce and immobilize (with low profile head bone screws and hemispherical head underside) a bone fracture in the maxilla of a patient. Because the square holes of the strip are chamfered in arcuate uniform inward configuration about the entire periphery of the holes, bending and shaping of the strip does not adversely affect the desired congruent fitment of the bone screws (seated through the strip) to the strip holes to effect affixation of the strip to the underlying bone structure.

While the invention has been described in connection with a particular structural embodiment of a perforated metallic strip, with perforations comprising a multiplicity of substantially square chamfered holes arranged in rows and lines, for internal fixation of bone fractures and for reconstructive surgery, many modifications of the invention will be apparent to those skilled in the art. Accordingly, such modifications are to be included within the spirit and scope of the invention as defined by the following claims.

What I claim is:

1. A pliable metallic perforated mesh plate structure for use with bone screws having a screw head including a hemispherical underside portion and a low profile upper portion for the internal fixation of fractures and for use in orthognathic and reconstructive surgery, said perforated mesh plate structure having a face side and a bone interface side and including a multiplicity of substantially square perforations arranged uniformly in rows and lines, and said substantially square perforations each including an arcuate chamfer extending inwardly from the face side of said mesh plate structure to the bone interface side of said mesh plate structure in substantially uniform configuration about the entire periphery thereof.

2. A pliable metallic perforated mesh plate structure for use with bone screws having a screw head including a hemispherical underside portion and a low profile upper portion for the internal fixation of fractures and for use in orthognathic and reconstructive surgery as claimed in claim 1 wherein said metallic perforated mesh plate structure is fabricated of biocompatible metals and metal alloys selected from the group consisting of titanium, titanium alloys, cobalt-chrome alloys and stainless steel.

3. A pliable metallic perforated implant plate structure having an outer face side and a bone interface side for use with bone screws having a screw head including a hemispherical underside portion and a low profile upper portion for the internal fixation of bone fractures and for use in orthognathic and reconstructive surgery, said perforated plate structure including a multiplicity of substantially square perforations extending from its outer face side to its bone interface side and arranged uniformly in parallel rows and parallel lines perpendicular to said rows, and said substantially square perforations each including an arcuate chamfer extending inwardly from the outer face side of said plate structure to the bone interface side of said plate structure in substantially uniform configuration about the entire periphery thereof.

4. A pliable metallic perforated implant plate structure having an outer face side and a bone interface side for use with bone screws having a screw head including a hemispherical underside portion and a low profile upper portion for the internal fixation of bone fractures and for use in orthognathic and reconstructive surgery as claimed in claim 3 wherein said metallic perforated plate structure is fabricated of biocompatible metal and metal alloys selected from the group consisting of titanium, titanium alloys, cobalt-chrome alloys and stainless steel.

* * * * *